558-293 SP
9/9/86 XR RE 32,246

United States Patent [19]
Horodysky

[11] E Patent Number: Re. 32,246
[45] Reissued Date of Patent: Sep. 9, 1986

[54] BORATED EPOXIDES AND LUBRICANTS CONTAINING SAME

[75] Inventor: Andrew G. Horodysky, Cherry Hill, N.J.

[73] Assignee: Mobil Oil Corporation, New York, N.Y.

[21] Appl. No.: 792,351

[22] Filed: Oct. 29, 1985

Related U.S. Patent Documents

Reissue of:
[64] Patent No.: 4,410,438
Issued: Oct. 18, 1983
Appl. No.: 329,774
Filed: Dec. 11, 1981

[51] Int. Cl.[4] ..... C10M 1/20; C10M 1/54
[52] U.S. Cl. ..... 252/49.6; 44/76; 549/213; 558/293; 558/296
[58] Field of Search ..... 252/49.6, 52 A; 260/462 R, 462 C; 549/213

[56] References Cited

U.S. PATENT DOCUMENTS

| | | | |
|---|---|---|---|
| 2,795,548 | 6/1957 | Thomas et al. | 252/49.6 |
| 3,205,240 | 9/1965 | Shepherd | 260/462 C X |
| 3,316,287 | 4/1967 | Nunn, Jr. et al. | 260/462 |
| 3,395,171 | 7/1968 | Drinkard, Jr. | 260/462 R |
| 3,625,899 | 12/1971 | Sawyer et al. | 252/75 |
| 4,104,374 | 8/1978 | Reuther et al. | 260/462 R |
| 4,370,248 | 1/1984 | Horodysky et al. | 252/49.6 |
| 4,374,032 | 2/1983 | Gemmill et al. | 252/49.6 |
| 4,563,293 | 1/1986 | Small, Jr. | 252/32.7 E |

FOREIGN PATENT DOCUMENTS

| | | | |
|---|---|---|---|
| 48-14627 | 2/1973 | Japan . | |
| 754874 | 8/1956 | United Kingdom | 49.6/ |

OTHER PUBLICATIONS

Mobil Docket 1263, U.S. Patent Application Ser. No. 304,482, filed 9/22/81.
SAE Technical Paper Series 800436 The Performance of Fuel-Saving Engine Oils, J. R. Lohuis, J. A. Murphy and T. W. Rogers.

*Primary Examiner*—W. J. Shine
*Attorney, Agent, or Firm*—A. J. McKillop; M. G. Gilman; L. P. Hobbes

[57] ABSTRACT

Lubricant and liquid fuel compositions containing a product made by reacting a boronating agent with a hydrocarbyl epoxide are provided. The invention also provides the product per se.

19 Claims, No Drawings

BORATED EPOXIDES AND LUBRICANTS CONTAINING SAME

Matter enclosed in heavy brackets [ ] appears in the original patent but forms no part of this reissue specification; matter printed in italics indicates the additions made by reissue.

BACKGROUND OF THE INVENTION

1. Field of the Invention

The invention is concerned with a novel group of compounds and their use in lubricants or liquid fuels as friction reducers, antioxidants or antiwear corrosivity redcers (e.g., copper corrosion reducers).

2. Discussion of the Prior Art

It is known that sliding or rubbing metal or other solid surfaces are subject to wear under conditions of extreme pressure. Wearing is particularly acute in modern engines in which high temperatures and contact pressures are prevalent. Under such conditions, severe erosion of metal surfaces can take place even with present generation lubricants unless a load carrying or antiwear additive is present herein.

Friction is also a problem any time two surfaces are in sliding or rubbing contact. It is of especial significance in an internal combustion engine and related power train components, because loss of a substantial amount of the theoretical mileage possible from a gallon of fuel is traceable directly to fraction.

With respect to the novel compounds of this invention, no art is known that teaches or suggests them. However, certain forms of epoxides have been used in lubricants. For example, U.S. Pat. No. 4,244,829 describes the use of epoxidized fatty acid esters as lubricity agents in lubricating oils.

SUMMARY OF THE INVENTION

In accordance with the invention, there is provided a lubricant composition containing a compound prepared by reacting an epoxide of the formula

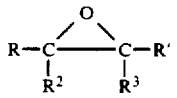

wherein R, R', $R^2$ and $R^3$ are hydrogen or a $C_8$–$C_{30}$ hydrocarbyl group, at least one of which is hydrocarbyl, with boric acid, boric oxide or an alkyl borate of the formula $$(RO)_xB(OH)_y$$

wherein x is 1 to 3 and y is 0 to 2, their sum being 3, or a boric oxide and R is an alkyl group containing from 1 to 6 carbon atoms.

The invention also provides a lubricant or liquid hydrocarbon fuel composition comprising a lubricant or fuel and a friction reducing amount of the product. It is further contemplated that the product will aid in the reduction of fuel consumption in an internal combustion engine.

DESCRIPTION OF THE SPECIFIC EMBODIMENTS

As has been mentioned hereinabove, the compounds of this invention can be made by reacting an epoxide with boric acid or an alkyl borate. They are primarily borate esters. Among possible other products present are the products of reaction between epoxide dimers, or higher oligomers, with a boron compound to form the corresponding borate esters. Included within the scope of the epoxides as set forth above, are 1,2-epoxydecane, 1,2-epoxydodecane, 1,2-epoxytetradecane, 1,2-epoxypentadecane, 1,2-epoxyhexadecane, 1,2-epoxyheptadecane, 1,2-epoxyoctadecane, 1,2-epoxyeicosane and mixtures of such epoxides. Hydrocarbyl is meant to include alkyl, aryl, cycloalkyl or cycloalkenyl groups containing from 8 to 30 carbon atoms, preferably 10 to 22 carbon atoms. Preferably, hydrocarbyl is an alkyl group.

As noted hereinabove, the boron compound used is boric acid, boric oxide or an alkyl borate, preferably boric acid. The latter includes the mono-, di- and trialkyl borates, such as the mono- di and triethyl borates.

The reaction, can be carried out at from about 80° C. to about 260° C., preferably from about 110° C. to about 180° C. The temperature chosen will depend for the most part on the particular reactants and on whether or not a solvent is used. In carrying out this reaction, it is preferable that quantities of reactants be chosen such that the molar ratio of epoxide to boron compound be from about 0.2 to about 4 to 1, preferably from about 0.5 to 1 to about 2 to 1. For example, in the reaction illustrated, in Example 1 the molar ratio is about 3 to 2. The epoxide can be partially borated, or reacted with an excess of the boronating species to form a composition containing from about 0.1% by weight of boron to as much as 10% boron or more.

While atmospheric pressure is generally preferred, the reaction can be advantageously run at from about 1 to about 5 atmospheres. Furthermore, where conditions warrant it, a solvent may be used. In general, any relatively non-polar, unreactive solvent can be used, including benzene, toluene, xylene and 1,4-dioxane. Other hydrocarbon and alcoholic soluents, which include propanol, butanol and the like, can be used. Mixtures of alcoholic and hydrocarbon solvents can be used also.

The times for the reactions are not critical. Thus, any phase of the process can be carried out in from about 1 to about 20 hours.

Of particular significance, in accordance with the present invention, is the ability to improve the resistance to oxidation and corrosion and high temperature resistance properties of oleaginous materials such as lubricating media which may comprise liquid oils, in the form of either a mineral oil or a synthetic oil, or mixtures thereof, or in the form of a grease in which any of the aforementioned oils are employed as a vehicle. In general, mineral oils, both paraffinic, naphthenic and mixtures thereof, employed as the lubricant, or grease vehicle, may be of any suitable lubricating viscosity range, for example, from about 45 SSU at 100° F. to about 6000 SSU at 100° F., and preferably from about 50 to about 250 SSU at 210° F. These oils may have viscosity indexes ranging to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of thickening agents can be used in the grease of this invention. Included among the thickening agents are alkali and alkaline earth metal soaps of fatty acids and fatty materials having from 12 to about 30 carbon atoms per molecule. The metals are typified by sodium, lithium calcium and barium. Fatty materials are illustrated by stearic acid, hydroxy-stearic acid, stearin, cottonseed oil acids, oleic acid, palmitic acid, myristic acid and hydrogenated fish oils.

Other thickening agents include salt and salt-soap complexes as calcium stearate-acetate (U.S. Pat. No. 2,197,263), barium stearate acetate (U.S. Pat. No. 2,564,561), calcium, stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Another group of thickening agents comprises substituted ureas, phthalocyamines, indanthrene, pigments such as perylimides, pyromellitdiimides, and ammeline.

The preferred thickening gelling agents employed in the grease compositions are essentially hydrophobic clays. Such thickening agents can be prepared from clays which are initially hydrophilic in character, but which have been converted into a hydrophobic condition by the introduction of long-chain hydrocarbon radicals into the surface of the clay particles; prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention.

In instances where synthetic oils are desired for any purpose herein, in preference to mineral oils, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl)ether, phenoxy phenylethers.

It is to be understood, however, that the lubricant compositions contemplated herein can also contain other materials. For example, corrosion inhibitors, extreme pressure agents, viscosity index improvers, coantioxidants, antiwear agents and the like can be used, including but not limited to phenates, sulfonates, succinimides, zinc dialkyl dithiophosphates, sulfurized olefins, chlorinated hydrocarbons, overbased calcium and/or magnesium compositions, hindered phenols, amine antioxidants, and the like. These materials do not detract from the value of the compositions of this invention; rather the materials serve to impart their customary properties to the particular compositions in which they are incorporated.

Mineral oil heat exchange fluids particularly contemplated in accordance with the present invention have the following characteristics: high thermal stability, high initial boiling point, low viscosity, high heat-carrying ability and low corrosion tendency.

Further, the transmission fluids of consequence to the present invention are blends of highly refined petroleum base oils combined with VI improvers, detergents, defoamants and special additives to provide controlled-friction or lubricity characteristics. Varied transmission design concepts have led to the need for fluids with markedly different frictional characteristics, so that a single fluid cannot satisfy all requirements. The fluids intended for use in passenger car and light-duty truck automatic transmissions are defined in the ASTM Research Report D-2; RR 1005 on "Automatic Transmission Fluid/Power Transmission Fluid Property and Performance Definitions." Specifications for low-temperature and aircraft fluids are defined in U.S. Government Specification MIL-H-5606A.

In addition, the oxidation and corrosion resistance, especially at elevated temperatures, of functional fluids such as hydraulic fluids can be improved by the adducts of the present invention.

The fuels that may be used for the purposes of this invention include (1) liquid hydrocarbon fuel, such as diesel oil, fuel oil and gasoline, (2) alcohol fuels such as methanol and ethanol and (3) mixtures thereof.

In general, the reaction products of the present invention may be employed in any amount which is effective for imparting the desired degree of friction reduction or antiwear activity or antioxidant activity, high temperature stability or antirust activity. In many applications, however, the product is effectively employed in amounts from about 0.01% to about 10% by weight, and preferably from about 1% to about 5% of the total weight of the composition.

The following Examples will present illustrations of the invention. They are illustrative only, and are not meant to limit the invention.

EXAMPLE 1

Borated 1,2-Epoxy-mixed $C_{15}$–$C_{18}$ Alkanes

Approximately 244 g of 1,2-epoxy-mixed $C_{15}$–$C_{18}$ alkanes (commercially available as Viking Chemical Company Vikolox 15–18 and containing the following 11,2-epoxyalkanes: 1,2-epoxy $C_{15}$ alkane—28%; 1,2-epoxy $C_{16}$ alkane—28%, 1,2-epoxy $C_{17}$ alkane—28%; 1,2-epoxy $C_{18}$ alkane—16%), 100 g of toluene and 42 g of boric acid were charged to a 1 liter reactor equipped with agitator, heater and Dean-Stark tube with condenser. The contents were heated up to 155° C. with agitation and $N_2$ purge of vapor space over a period of about 5 hours until water evolution stopped. The solvent was removed by vacuum distillation at 155° C. and the product was filtered at about 120° C. through diatomaceous earth. The product became a clear, amber colored, gel-like waxy solid upon cooling.

EXAMPLE 2

Borated 1,2-Epoxytetradecane

Approximately 212 g of 1,2-epoxytetradecane (obtained commercially as Viking Chemical Company Vikolox 14), 100 g of toluene solvent and 42 g of boric acid were charged to a 1 liter reactor equipped as described in Example 1. The contents were heated up to 160° C. with agitation and $N_2$ purge of vapor space until water evolution stopped over a period of 6 hours. The solvent was removed by vacuum distillation at 160° C. and the product was filtered through diatomaceous earth. The product was a clear pale viscous fluid and became a waxy solid upon cooling.

EXAMPLE 3

Borated 1,2-Epoxyhexadecane

Approximately 1440 g of 1,2-epoxyhexadecane (obtained commercially from Union Carbide), 400 g of toluene and 248 g of boric acid were charged to a 5 liter reactor equipped as described in Example 1. The contents were heated up to 180° with agitation and $N_2$ was used to purge the vapor space until water evolution stopped. This took place over a period of 5 hours. The solvent was removed by vacuum distillation at 180° C., and the product was filtered at about 120° C. through diatomaceous earth. The product became an amber waxy solid upon cooling.

EXAMPLE 4

Borated 1,2-Expoxyhexadecane 1,2-Epoxyhexadecane was borated as generally described in Example 3, except that the following ratio of reactants was used: 1440 g of 1,2-epoxyhexadecane, 500 g of toluene and 375 g of boric acid. The product cooled to form an amber waxy solid.

EXAMPLE 5

Highly Borated 1,2-Epoxy-Mixed $C_{15}$–$C_{18}$ Alkanes

Approximately 366 g of 1,2-epoxy-mixed $C_{15}$–$C_{18}$ alkanes (as described in Example 1), 250 g of toluene, 380 g of diluent process oil and 188 g of boric acid were charged to a reactor equipped as described in Example 1. The contents were heated up to about 170° C. with agitation and $N_2$ purge of the vapor space until water evolution stopped, i.e., over a period of 5 hours. The solvent was removed by vacuum distillation and the product was filtered through diatomaceous earth. The product become waxy upon cooling.

EXAMPLE 6

Highly Borated 1,2-Epoxy-Mixed $C_{15}$–$C_{18}$ Alkanes 1,2-epoxy-mixed $C_{15}$–$C_{18}$ alkanes were borated as generally described in Example 5 except that the following reactants were used: 366 g of 1,2-epoxy-mixed $C_{15}$–$C_{18}$ alkanes, 400 g of toluene, 435 g of diluent process oil, 252 g of boric acid, and 10 ml of butanol. The product became somewhat waxy upon cooling.

EVALUATION OF THE COMPOUNDS

The compounds were evaluated in a low Velocity Friction Apparatus (LVFA) in a fully formulated 5W-20 synthetic automotive engine oil containing an additive package including antioxidant, dispersant and detergent. The test compounds were used at 1%, 2% and 4% by weight of the total weight of oil.

Description

The Low Velocity Friction Apparatus (LVFA) is used to measure the coefficient of friction of test lubricants under various loads, temperatures, and sliding speeds. The LVFA consists of a flat SAE 1020 steel surface (diameter 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gague output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

Procedure

The rubbing surfaces and 12–13 ml of test lubricants are placed on the LVFA. A 240 psi load is applied, and the sliding speed is maintained at 40 fpm at ambient temperature for a few minutes. A plot of coefficients of friction ($U_k$) vs. speed were taken at 240, 300, 400, and 500 psi. Freshly polished steel specimens are used for each run. The surface of the steel is parallel ground to 4 to 8 microinches. The results in Table 1 refer to percent reduction in friction compared to the unmodified oil. That is, the formulation mentioned above was tested without the compound of this invention and this became the basis for comparison. The results were obtained at 250° F. and 500 psi.

TABLE 1

Friction Test Results Using Low Velocity Friction Apparatus

| Additive | Additive Conc. in Base Blend, Wt. % | % Reduction in Coefficient of Friction in LVFA at 5 Ft./Min. | 30 Ft./Min. |
|---|---|---|---|
| Base Blend-Fully Formulated Engine Oil | — | 0 | 0 |
| Example 1 | 2 | 19 | 11 |
| Example 2 | 2 | 15 | 9 |
| Example 3 | 2 | 13 | 7 |
| Example 5 | 4 | 30 | 22 |
| Example 6 | 4 | 32 | 24 |
| | 2 | 31 | 26 |
| | 1 | 34 | 31 |

Also, copper strip corrosion tests were run in accordance with ASTM D130–80, the results of which are shown in Table 2. Effective corrosion inhibition was observed in 200" solvent paraffinic neutral mineral oil.

TABLE 2

Copper Strip Corrosivity Test Using ASTM D130-80

| Additive | Additive, Wt. % | 210° F., 6 Hrs. | 250° F., 3 Hrs. |
|---|---|---|---|
| Example 1 | ½ | 1A | 1A |
| | 1 | 1A | 1A |
| Example 3 | ½ | 1A | 1A |
| | 1 | 1A | 1A |
| Example 4 | ½ | 1A | 1A |
| | 1 | 1A | 1A |

The products were further evaluated for oxidation stability. In most cases, improvements in oxidative stability over the base oil were observed. Basically, the test lubricant is subjected to a stream of air which is bubbled through at the rate of 5 liters per hour at 425° F. for 24 hours. Present in the composition are samples of metals commonly used in engine construction, namely, iron, copper, aluminum, and lead. See U.S. Pat. No. 3,682,980, incorporated herein by reference, for further details of the test. Improvements in viscosity index or neutralization number (or both) show effective control. See results in Table 3.

TABLE 3

| | Catalytic Oxidation Test 40 hours @ 325° F. | | | |
|---|---|---|---|---|
| | Additive Conc. Wt %, | % Inc. in Visc. of Oxidized Oil Using KV @ 210° F. | Neutral Number NN | Lead Loss mg |
| Base Oil-0% Additive, 200" Solvent Paraffinic Neutral Lubricating Oil | | 67 | 3.62 | −1.2 |
| Example 1 | ½ | 22 | 2.45 | 0.1 |
| | 1 | 25 | 2.36 | 0.0 |
| Example 3 | ½ | 14 | 1.43 | 0.0 |
| | 1 | 14 | 1.53 | 0.0 |
| Example 4 | ½ | 11 | 1.52 | 0.0 |
| | 1 | 6 | 0.98 | 0.0 |

I claim:

1. A product of reaction made by reacting (1) an epoxide of the formula

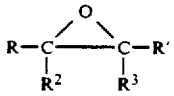

wherein R, R', $R^2$ and $R^3$ are hydrogen or hydrocarbyl groups containing from 8 to 30 carbon atoms, at least one of which is hydrocarbyl, with (2) a boron compound selected from boric acid, boric oxide and an alkyl borate of the formula $$(RO)_xB(OH)_y$$

wherein x is 1 to 3, y is 0 to 2, their sum being 3, and R is an alkyl group having 1 to 6 carbon atoms, the reaction being carried out at from about 80° C. to about 260° C. using a molar ratio of epoxide to boron compound of from about 0.2 to 1 to about [4] *1.5* to 1, respectively.

2. The product of claim 1 wherein the hydrocarbyl group is an alkyl, aryl, cycloalkyl or cycloalkenyl.

3. The product of claim 1 wherein the epoxide is 1,2-epoxydecane, 1,2-epoxydodecane, 1,2-epoxytetradecane, 1,2-epoxypentadecane, 1,2-epoxyhexadecane, 1,2-epoxyheptadecane, 1,2-epoxyoctadecane, 1,2-epoxyeicosane and mixtures thereof.

4. The product of claim 1 wherein the epoxide is reacted with boric acid.

5. The product of claim 1 wherein the epoxide is 1,2-epoxy-mixed $C_{15}$–$C_{18}$ alkanes and the boron compound is boric acid.

6. The product of claim 1 wherein the epoxide is 1,2-epoxytetradecane and the boron compound is boric acid.

7. The product of claim 1 wherein the epoxide is 1,2-epoxyhexadecane and the boron compound is boric acid.

8. A lubricant composition comprising a major amount of an oil of lubricating viscosity or a grease therefrom and an anti-friction amount of a product of reaction made by reacting (1) an epoxide of the formula

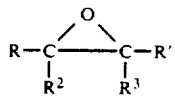

wherein R, R', $R^2$ and $R^3$ are hydrogen or hydrocarbyl groups containing from 8 to 30 carbon atoms, at least one of which is hydrocarbyl, with (2) a boron compound selected from boric acid, boric oxide and an alkyl borate of the formula $$(RO)_xB(OH)_y$$

wherein x is 1 to 3, y is 0 to 2, their sum being 3, and R is an alkyl group having 1 to 6 carbon atoms, the reaction being carried out at from about 80° C. to about 260° C. using a molar ratio of epoxide to boron compound of from about 0.2 to 1 to about 4 to 1, respectively.

9. The composition of claim 8 wherein in the product the hydrocarbyl group is an alkyl, aryl, cycloalkyl or cycloalkenyl group.

10. The composition of claim 8 wherein in the product the epoxide is 1,2-epoxydecane, 1,2-epoxydodecane, 1,2-epoxytetradecane 1,2-epoxypentadecane, 1,2-epoxyhexadecane, 1,2-epoxyheptadecane, 1,2-epoxyoctadecane, 1,2-epoxyeicosane or mixtures thereof.

11. The composition of claim 8 wherein the product is made by reacting the epoxide with boric acid.

12. The composition of claim 8 wherein the product is made by reacting 1,2-epoxy-mixed $C_{15}$–$C_{18}$ alkanes with boric acid.

13. The composition of claim 1 wherein the product is made by reacting 1,2-epoxytetradecane with boric acid.

14. The composition of claim 8 wherein the product is made by reacting 1,2-epoxyhexadecane with boric acid.

15. The composition of claims 8, 9, 10, 11, 12, 13 or 14 wherein the oil is (1) a mineral oil, (2) a synthetic oil, (3) mixtures of (1) and (2) or (4) a grease of (1), (2) or (3).

16. The composition of claim 15 wherein the oil is a mineral oil.

17. The composition of claim 15 wherein the oil is a synthetic oil.

18. The composition of claim 8 wherein the lubricant is a grease.

19. The composition of claim 8 wherein the oil is a mixture of mineral and synthetic oils.

* * * * *